United States Patent [19]

Stapp

[11] 4,237,331

[45] Dec. 2, 1980

[54] OLEFIN OXIDATION PROCESS

[75] Inventor: Paul R. Stapp, Bartlesville, Okla.

[73] Assignee: Phillips Petroleum Company, Bartlesville, Okla.

[21] Appl. No.: 88,717

[22] Filed: Oct. 26, 1979

Related U.S. Application Data

[62] Division of Ser. No. 895,339, Apr. 11, 1978.

[51] Int. Cl.³ ............................................. C07C 7/152
[52] U.S. Cl. ...................................... 585/845; 568/401; 585/850
[58] Field of Search ................................ 585/845, 850

[56] References Cited

U.S. PATENT DOCUMENTS

| | | | |
|---|---|---|---|
| 3,122,586 | 2/1964 | Berndt et al. | 260/597 B |
| 3,154,586 | 10/1964 | Bander et al. | 260/597 B |
| 3,365,498 | 1/1968 | Bryan et al. | 260/586 |
| 3,397,250 | 8/1968 | Nambu | 568/895 |
| 3,518,323 | 6/1970 | Pine et al. | 585/850 |
| 3,527,829 | 9/1970 | Horie et al. | 585/850 |
| 3,609,180 | 9/1971 | Shigematsu et al. | 260/497 A |
| 3,701,810 | 10/1972 | Hasegawa et al. | 260/597 B |
| 3,979,474 | 9/1976 | Zerrweck | 585/329 |

OTHER PUBLICATIONS

Chem. Abs. 83, 178203v (1975).
Encyclopedia of Chemical Technology, Kirk–Othmer, vol. 3, (1964), pp. 830–865.

*Primary Examiner*—C. Davis

[57] ABSTRACT

Olefins are oxidized to carbonyl compounds, for example, 2-hexene to a mixture of 2-hexanone and 3-hexanone, with a palladium/copper/boric acid catalyst and a suitable surfactant or phase transfer agent. The reaction takes place in a diluent system comprising at least two liquid phases, wherein at least one liquid phase is an aqueous phase, and in the presence of free oxygen. The catalyst system can be used to oxidize internal olefins, as well as terminal olefins, at reasonable rates. The catalyst system can also be used for the selective oxidation of linear olefins in a mixed stream containing linear and branched olefins.

10 Claims, No Drawings

OLEFIN OXIDATION PROCESS

BACKGROUND OF THE INVENTION

This application is a divisional of my copending application Ser. No. 895,339, filed Apr. 11, 1978, now allowed.

This invention relates to the oxidation of olefinic carbon-carbon double bonds to carbonyl groups. In another aspect, it relates to the oxidation of mono-olefins to a carbonyl compound, preferably a ketone. In another aspect, this invention relates to an oxidation process using a diluent system comprising at least two liquid phases with at least one being aqueous. In another aspect, it relates to the use of a two-phase diluent system with one being an aqueous phase and the other being an organic phase. In another aspect, this invention relates to a novel catalyst, namely, a palladium/copper/boric acid catalyst, for the oxidation of olefinic carbon-carbon double bonds to carbonyl groups. In yet another aspect, this invention relates to the use of a palladium/copper/boric acid catalyst in conjunction with a multiphase diluent system and a surfactant for the oxidation of olefinic carbon-carbon double bonds to carbonyl groups. In another aspect, this invention relates to a process for oxidizing internal, as well as terminal mono-olefins, to a carbonyl compound in a multiphase system. In sitll another aspect, this invention relates to a low-corrosion catalyst system for the oxidation of olefinic groups to carbonyl groups. This invention also relates to a process for separating isobutylene from a mixed stream of $C_4$ olefins. In another aspect, this invention relates to a process for producing methyl ethyl ketone in which an inexpensive $C_4$ feed stream having a mixture of $C_4$ olefins can be used.

The Wacker-type oxidation of ethylene to acetaldehyde using a palladium chloride/cupric chloride/hydrochloric acid catalyst in an aqueous solution has been modified and applied to the synthesis of methyl ketones from terminal olefins. However, major problems have been encountered in using the Wacker-type oxidation in the oxidation of higher olefins. One problem is that of reduced rates of reaction due to the low solubility of the olefin in the aqueous medium. Another major problem is the concomitant secondary oxidation of the ketone product which leads to poor selectivily and poor yield of desired product.

Various methods have attempted to increase the conversion and selectivity of olefins in an oxidation process, however, these methods have only been effective for the oxidation of terminal olefins and have been relatively ineffective for the oxidation of internal olefins. The use of such a system would require that only terminal olefins be used in a feed stream for the synthesis, for example, of methyl ethyl ketone from a $C_4$ olefin, with separation of the internal olefins either before or after the reaction. If both terminal and internal olefins were able to be oxidized at a reasonable rate, however, expensive separation steps would be necessary and an inexpensive feed stream of a mixture of butenes, both 1- and 2-butenes, could be used to synthesize methyl ethyl ketone. Furthermore, if the catalyst system used in the oxidation process selectively oxidized only the linear olefins in a mixed stream containing linear and branched olefins, the process can be used for the simultaneous production of methyl ethyl ketone and separation of isobutylene from a stream comprising a mixture of linear butenes and isobutylene. Also, if isobutylene was not oxidized in the presence of the catalyst system, as opposed to prior art catalyst systems which oxidize isobutylene, relatively pure isobutylene can be recovered.

Corrosion of process equipment is also a problem when a catalyst containing halide ions is utilized in the oxidation process, a low-corrosion catalyst can be desirable at times.

An object of the present invention, therefore, is to increase the conversion and selectivity of olefins in an oxidation process.

Another object is to provide an oxidation process for olefins causing little corrosion to the process equipment.

Another object is to provide for a more economical and simplified process for the manufacture of methyl ethyl ketone.

Still another object of the present invention is to provide an improved process for the purification of isobutylene when contained in a stream of linear butenes.

Yet another object is to provide an oxidation process which oxidizes internal olefins at reasonable rates.

Other objects, aspects, and the several advantages of this invention will be apparent to those skilled in the art upon a study of this disclosure and the appended claims.

SUMMARY OF THE INVENTION

The instant invention is concerned with a process for the conversion of olefinic carbon-carbon double bonds to carbonyl groups by oxidation of olefinic compounds in a reaction system comprising at least two liquid phases wherein at least one liquid phase is an aqueous phase. The olefinic hydrocarbon reactant is oxidized in the presence of free oxygen, a catalyst, a surfactant, and a multiphase diluent system which is preferably a two-phase system with one phase aqueous and the other organic. The catalyst is a palladium/copper/boric acid catalyst with the palladium being either palladium metal or palladium compound, the copper being either a cuprous or cupric compound or a mixture thereof, and the boric acid comprising any boron-containing material that provides a catalytically active boric acid under the conditions employed in the reaction.

In another embodiment, a catalyst system comprising palladium acetate, cupric acetate and boric acid is utilized. This catalyst system has the advantage of a very low level of ionic halide and consequently would allow the use of less expensive reactors because corrosion problems would not be severe.

In another embodiment, a catalyst system of palladium/copper/boric acid, e.g., orthoboric acid, is used in a two-phase diluent to selectively oxidize linear butenes in a $C_4$ stream to carbonyl compounds without affecting isobutylene. The catalyst system oxidizes both terminal and internal butenes yet does not oxidize isobutylene. This allows the use of an inexpensive and readily available $C_4$ stream as feed for the production of methyl ethyl ketone.

In another embodiment, isobutylene is separated from a mixture of isobutylene and linear butenes by selectively oxidizing the linear butenes to carbonyl compounds with a palladium/copper/boric acid catalyst in a two-phase system.

DETAILED DESCRIPTION OF THE INVENTION

The instant invention is concerned with a process and catalyst for the conversion of olefinic carbon-carbon double bonds to carbonyl groups, preferably ketones, by oxidation of said olefinic compound in a reaction system comprising at least two liquid phases wherein at least one liquid phase is an aqueous phase. The reaction takes place in the presence of a phase-transfer agent, herein referred to as a surfactant, and free oxygen. This invention is also concerned with a process for the selective oxidation of the linear olefins in a mixed stream containing linear and branched olefins.

I. OLEFINIC HYDROCARBON REACTANT

The olefinic hydrocarbon reactant which is oxidized according to the process of the instant invention can be any suitable olefin with one olefinic double bond per molecule. The preferred olefinic reactant, however, is selected from the groups consisting of acyclic olefinic compounds containing from 3–20 carbon atoms per molecule and having one olefinic carbon-carbon double bond per molecule, and cyclic olefinic compounds containing from 5–7 carbon atoms per molecule and having one olefinic carbon-carbon double bond per molecule. Within the limitations described above, suitable olefinic hydrocarbon reactants can be represented by the general formula RCH=CHR' wherein R and R' are selected from the group consisting of hydrogen, alkyl, and cycloalkyl radicals and wherein R can be the same or different from R' and wherein R and R' taken together can form an alkylene radical thus forming a cyclic system. The term "olefinic carbon-carbon double bond" as used herein is not meant to include those carbon-carbon double bonds which are part of an aromatic carbocyclic system of alternating single and double bonds.

Examples of preferred mono-olefinic compounds include: propylene, 1-butene, 2-butene, 1-pentene, 2-pentene, 1-hexene, 2-hexene, 3-hexene, 1-octene, 1-decene, 1-dodecene, 1-hexadecene, 1-octadecene, 1-eicosene, vinyl cyclohexane, cyclopentene, cyclohexene, cycloheptene, 3,3-dimethyl-1-butene, and the like, and mixtures thereof.

The oxidation reaction of this invention has been found to have a high selectivity for the oxidation of olefins of the general formula described above with very little oxidation of gem-disubstituted olefins such as isobutylene. For example, a $C_4$ refinery stream containing 1-butene, cis-2-butene, trans-2-butene, and isobutylene can be oxidized to methyl ethyl ketone with very little oxidation of the isobutylene.

This is a significant improvement over prior art system which oxidize the isobutylene to yield a complex mixture of products. For example, the oxidation catalyst systems employed in U.S. Pat. No. 3,154,586 and U.S. Pat. No. 3,701,810 convert isobutylene to isobutyraldehyde and t-butyl alcohol.

The oxidation reaction of this invention also provides a method of separating isobutylene from a $C_4$ stream by selectively oxidizing the linear olefins to leave the pure isobutylene. Such a purification procedure is an improvement over the conventional purification which involves the hydration of isobutylene to 2-methyl-2-propanol, separation of the 2-methyl-2-propanol from the butenes, and dehydration of 2-methyl-2-propanol to yield isobutylene.

Since the process oxidizes internal as well as terminal olefins, the process can also be used for the oxidation of a mixture of hexenes. The oxidation of hexenes yields mixtures of hexanones which are useful as paint thinners and solvents.

II. CATALYST SYSTEM

The catalyst utilized according to the instant invention for the oxidation of olefinic hydrocarbons to carbonyl compounds is made up of three components: (1) a palladium component, (2) a copper component, and (3) a boric acid component.

(1) Palladium Component

The palladium component of the catalyst system of the instant invention can be palladium metal such as finely divided palladium powder or a palladium compound. Examples of suitable palladium compounds include allyl palladium chloride dimer $[C_3H_5PdCl]_2$, dichlorobis (triphenylphosphine) palladium(II), palladium(II) acetate, palladium(II) acetylacetonate, tetrakis(triphenylphosphine) palladium(O), palladium(II) chloride, palladium(II) iodide, palladium(II) nitrate, and the like. Mixtures of the above palladium compounds can also be utilized as the palladium component of the instant catalyst system if so desired.

(2) Copper Component

The copper component of the instant catalyst system can be provided by utilizing a cuprous or cupric compound or mixture thereof. A wide variety of copper compounds can be utilized to provide the copper component of the instant catalyst system. Specific examples of suitable copper compounds include copper(I) acetate, copper(II) acetate, copper(II) acetylacetonate, copper(I) bromide, copper(I) chloride, copper(II) chloride, copper(I) iodide, copper(II) nitrate, and the like.

(3) Boric Acid Component

The boric acid component of the catalyst system of this invention can be any boron-containing material that provides a catalytically active boric acid under the conditions of the oxidation reaction of this invention. Suitable boron-containing materials include boric acids, boron oxides, and boric acid esters. Specific examples of suitable boron components include orthoboric acid ($H_3BO_3$), metaboric acid ($HBO_2$), tetraboric acid ($H_2B_4O_7$), boron oxide ($B_2O_3$), triethyl borate, tributyl borate, and triphenyl borate. Orthoboric acid is the currently preferred boric acid component of this invention.

An optional component of the catalyst system of this invention is a halide of an alkali metal or an alkaline earth metal. Specific examples of suitable alkali metal halides include lithium chloride, lithium bromide, lithium iodide, sodium chloride, sodium bromide, sodium iodide, potassium chloride, rubidium chloride, cesium chloride, and the like. Examples of suitable alkaline earth metal halides include calcium chloride, calcium bromide, calcium iodide, barium chloride, and the like. Mixtures of the above metal halides can be employed as an optional component of the catalyst system if desired.

The ratios of the various catalyst components can be expressed in terms of a molar ratio of copper to palladium and a molar ratio of a boric acid or compound that forms a boric acid to palladium. The molar ratio of copper component to palladium component in the instant catalyst sytem is broadly from about 1/1 up to about 200/1 and preferably from about 2/1 up to about 50/1. As will be seen in the examples, the amount of boric acid used in the oxidation reaction of this invention can be varied widely. However, the molar ratio of boric acid or precursor thereof to palladium component will generally be from about 0.2/1 up to about 100/1 and preferably from about 5/1 up to about 25/1.

The amount of catalyst employed according to the instant invention can be expressed in terms of the molar ratio of olefinic hydrocarbon reactant to palladium component of the catalyst system. Broadly, the molar ratio of olefinic reactant to palladium component is from about 5/1 up to about 1,000/1 and preferably from about 10/1 up to about 250/1.

When a halide is to be used in the instant invention, the molar ratio of halide ion derived from the alkali metal or alkaline earth metal halide to palladium is broadly from about 5/1 to about 1,000/1 and preferably from about 20/1 up to about 400/1.

Another component of the reaction system according to the instant invention is a compound selected from one of the five groups to be described more fully below. It will be recognized from the description of the five groups of compounds below that said compounds generally would be expected to exhibit surface-active properties, and as such they may be called surfactants. However, the term surfactants encompasses a very broad class of compounds, and it has been discovered that not all surfactants are suitable for use in two-phase oxidations. Nevertheless, for convenience and simplicity, the suitable compounds that can be employed according to the instant invention and described more fully below will be termed surfactants herein. At the present time, it is not known whether these compounds behave as phase-transfer catalysts such as is taught in the art, or whether they are functioning as micellar catalysts, a feature also disclosed in the prior art. Because of this uncertainty in the mode of action of these compounds in the instant invention and for convenience as mentioned above, the following compounds will merely be described herein as surfactants.

A suitable surfactant for use in the reaction system of the instant invention is selected from one of the five following groups:

(A) Quaternary ammonium salts of the general formula $(R''')_4N^+X^-$ wherein each $R'''$ is selected from a group consisting of alkyl, aryl, alkaryl, and aralkyl radicals of from 1 to 20 carbon atoms, and wherein the total number of carbon atoms in said quaternary ammonium salt is from 8 to 30 carbon atoms broadly and preferably from 16 to 22 carbon atoms; and wherein $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms. It will be noted that a variety of anions are suitable as the $X^-$ component of the quaternary ammonium salts. Specific examples of quaternary ammonium salts according to the general formula given above include cetyltrimethylammonium (hexadecyltrimethylammonium) bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutylammonium fluoride, tetrabutylammonium tetrafluoroborate, and the like.

(B) Alkali metal alkyl sulfates of the general formula $R'^vOSO_3M$ wherein $R'^v$ is an alkyl radical of from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and the like.

(C) Alkali metal salts of alkanoic acids of the general formula $R'^vCO_2M$ wherein $R'^v$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and the like.

(D) Alkali metal salts of alkaryl sulfonic acids of the general formula

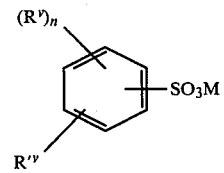

wherein $R'^v$ and M have the same meaning as given above and wherein $R^v$ is an alkyl radical of 1 to 4 carbon atoms and wherein n is 0 or an integer of from 1 to 4. Specific examples of compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzenesulfonate, sodium eicosylbenzenesulfonate, potassium dodecyltoluenesulfonate, sodium dodecylxylenesulfonate, and the like.

(E) 1-Alkyl pyridinium salts of the general formula

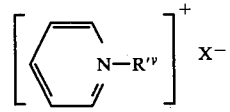

wherein $R'^v$ and $X^-$ have the same meaning as described above. Examples of suitable 1-alkyl pyridinium salts include 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio surfactant to palladium compound will be from about 0.01/1 to about 10/1 and preferably from about 0.1/1 to about 3/1.

III. DILUENT SYSTEM

As indicated above, the oxidation of the olefinic hydrocarbon according to the instant invention is carried out in the presence of a diluent comprised of at least two liquid phases (preferably only two) at least one of which is an aqueous phase.

The nonaqueous phase will hereinafter be termed the organic phase. Said organic phase should be relatively inert to the oxidation conditions, of course, and also relatively inert to hydrolysis-type reactions. Furthermore, it is apparent that if at least two phases are present, at least one of which is an aqueous phase, that the organic diluent utilized must have somewhat limited solubility in the aqueous phase. Within these general requirements, a rather broad range of organic compounds can be utilized to form the organic phase according to the instant invention. Generally speaking, suitable compounds can be found in the classes of compounds described as aromatic hydrocarbons or alkyl-substituted aromatic hydrocarbons, halogenated aromatic compounds and esters of aromatic carboxylic acids although the latter may be less preferred because of a tendency toward hydrolysis of the ester group in certain instances. Specific examples of suitable organic diluents include benzene, toluene, chlorobenzene, methyl benzoate, bromobenzene, 1,2,4-trichlorobenzene, orthodichlorobenzene, sulfolane, ortho-xylene, para-xylene, meta-xylene, dimethyl ortho-phthalate, and the like. Mixtures of the above organic diluents may be utilized in some cases as desired. Generally speaking, the choice of the organic diluent may be often determined based on the difference in boiling points expected between the product of the oxidation reaction and the organic diluent so as to facilitate separation of the components of the reaction mixture.

The amounts of aqueous phase and organic diluent phase based on the starting olefinic reactant can vary over a wide range, and a suitable broad range includes from 20 to 0.2 volumes of organic diluent per volume of olefinic hydrocarbon reactant and preferably from 5 to 1 volumes of organic diluent per volume of olefinic hydrocarbon reactant. Similarly, the broad range for the amount of aqueous phase is from 20 to 0.2 volumes per volume of olefinic hydrocarbon reactant and preferably from 5 to 1 volumes per volume of olefinic hydrocarbon reactant. It is worth pointing out some predictions relating to the expected effects of the volume of aqueous phase on the oxidation reaction of the instant invention. First, if the aqueous phase volume becomes too small the concentration of the catalyst components in the aqueous phase may cause an undesirable increase in viscosity or may cause undesirable solubility problems, thus greatly slowing down the reaction rate wherein the olefinic hydrocarbon reactant is oxidized to the desired carbonyl compound. Secondly, if the aqueous phase becomes too large, the concentration of catalyst components may be so dilute that the reaction with the olefinic hydrocarbon may also be greatly slowed. However, it can be seen that a judicious choice of the optimum amount of the aqueous phase for high conversion levels of the olefinic hydrocarbon reactant can readily be determined by a few well-chosen experiments.

At present, it is believed that the primary function of the organic phase in the reaction system of the instant invention is to greatly increase the selectivity to the desired carbonyl compound by effectively removing the carbonyl compound product from the locus of the oxidation reaction thereby preventing side reactions such as isomerization and/or further oxidation of the carbonyl compound. However, this explanation is to be treated merely as a theory of the mode of action of the organic phase in the reaction, and the instant invention should not be bound to any extent by said theory.

IV. OXYGEN

As indicated previously, the reaction of the instant invention is an oxidation reaction whereby an olefinic reactant is converted to a carbonyl compound in the presence of a catalyst and diluent system described above. Thus, the reaction of the instant invention is carried out in the presence of free oxygen. The oxygen may be supplied to the reaction mixture essentially as pure oxygen or admixed with other gases which are essentially inert to the reaction conditions. Air can be utilized as a source of oxygen for the oxidation reaction of this invention. As is generally true for most oxidation reactions, the reaction of the instant invention can be exothermic and thus some care should be exercised in the amount of oxygen present in the reaction system. For this reason and also to improve control of the temperature of the reaction, it is preferred to add oxygen or gaseous mixture containing oxygen to the reaction zone incrementally such that explosive ranges of oxygen concentration do not develop. The pressure of oxygen utilized for the instant invention can broadly be from 2 up to 250 psig and preferably from 10 to 100 psig above the autogenous pressure at the temperature utilized.

V. REACTION CONDITIONS

The temperature utilized with the catalyst system of this invention is broadly from 20° to about 200° C. and is especially useful in the temperature range of 65° to 150° C. It can also be noted that the particular temperature employed may be dependent somewhat on the olefinic hydrocarbon reactant. For example, at relatively high temperatures, a lower molecular weight olefinic hydrocarbon reactant may tend to be very insoluble in the aqueous phase of the two-phase system of the instant invention, thus causing a reduced conversion of the olefinic hydrocarbon reactant. On the other hand, a higher molecular weight olefinic reactant may be able to tolerate a higher reaction temperature and still maintain a reasonable degree of solubility in the aqueous phase and thus achieve a good degree of conversion at the higher temperature.

The time employed for the reaction according to the instant invention can vary over a wide range and will to some extent depend on the desired degree of conversion of the olefinic hydrocarbon reactant. Generally, a time period such as from 30 minutes to 8 hours will be employed in the instant invention.

Because the oxidation reaction according to the instant invention is carried out in the presence of a diluent system comprising at least two liquid phases, it is expected that good stirring will be of benefit and conventional means of achieving good agitation and contact between the liquid phases can be employed as taught by the prior art.

The charge order of the reaction components and catalyst components is not particularly critical in the process of the instant invention. However, the presence of oxygen in the reaction mixture prior to heating of the mixture to the desired reaction temperature appears to promote higher selectivity to the desired carbonyl compound.

The process of the instant invention can be carried out in either a batch or continuous process.

Reaction vessels utilized in the process of the instant invention should, of course, be able to withstand the oxidizing conditions which are present. For this reason, glass-lined, tantalum, or titanium clad vessels and conduits are recommended for use in the process of this invention.

VI. Reaction Mixture Workup

A variety of methods can be utilized to recover the products, unreacted olefinic hydrocarbon starting materials, and the catalyst in the aqueous phase in the instant invention. For example, the reaction mixture can be admixed with a saturated aqueous sodium chloride solution followed by extraction of the mixture into diethyl ether. The ether extract can then be distilled or treated in such a manner as to remove the ether leaving the organic residue containing the product and any unreacted olefinic hydrocarbon reactant. Said residue can then be subjected to fractional distillation procedures to recover the various components.

Another method of reaction mixture workup can involve fractional distillation of the entire reaction mixture to separate the components into various fractions, and said distillation kettle bottoms can be recycled to the reaction zone as that portion containing essentially all of the catalyst system for the reaction.

Another method of treating the reaction mixture is to contact the entire mixture with a lower alkane such as n-pentane, then separating the aqueous phase from the organic phase followed by fractional distillation of the organic phase to recover the products and any unreacted olefinic hydrocarbon reactants. The aqueous phase can be recycled to the reaction zone as described above since it contains essentially all of the catalyst components.

VII. PRODUCT UTILITY

As indicated earlier, the reaction of the instant invention provides a process for the conversion of olefinic hydrocarbon reactants to carbonyl compounds. Said carbonyl compounds are ketones. Ketones from the olefinic hydrocarbon reactants described in Part I above have generally well known utilities. For example, they can be utilized as solvents (methyl ethyl ketone) or as intermediates in the synthesis of other chemical compounds. (pinacolone).

The following examples serve to illustrate the invention, but they are not intended to limit it thereto:

VIII. EXAMPLES

In the runs that are described in Examples I through V with hexenes as the olefinic reactants, the reaction vessel utilized in each of the runs was a 250 ml Fischer-Porter aerosol compatibility bottle equipped with a magnetic stirrer. Generally, the bottle was charged with the catalyst system, the diluents and the olefinic reactant, after which the bottle was placed in an oil bath, pressured to about 30 psig with oxygen and then heated to about 105° C. During the 5-hour reaction period, the bottle was pressured intermittently at about 10–30 minute intervals to an oxygen pressure of about 80–120 psig. The reaction mixture was recovered from the bottle reactor by cooling the reactor, venting the gas phase, and pouring the mixture into about 500 ml of water. This mixture was then extracted into diethyl ether and the ether extract washed with water and dried over magnesium sulfate. The dried ether extract was then filtered and the ether stripped off in a distillation step. The residue remaining after the removal of the ether was then analyzed by gas-liquid phase chromatography (glc). Significant deviations from the above general procedures will be noted where appropriate in the respective examples that follow.

In the runs that are described in Examples VI through IX and XI to XII with various butenes as the olefinic reactants, the apparatus and procedure described above were generally followed (with some variations in reaction temperature) up to removal of the reaction mixture from the reactor. The reactor was cooled, vented, and cyclohexane was added as an internal standard for glc analysis of the unreacted butenes for a determination of olefin conversion. The reaction mixture was then poured into a saturated sodium chloride solution (50 ml), and the mixture was extracted continuously with diethyl ether for 24 hours. The ether extract was filtered and the ether was removed by distillation. The residue remaining after the removal of the ether was then analyzed by glc.

Example I

A series of runs was carried out in which 1-hexene was oxidized to 2-hexanone or to a mixture of 2-hexanone and 3-hexanone. In each run, the 250 ml Fischer-Porter aerosol compatibility bottle was charged with 16.8 g 1-hexene (200 mmoles), 0.9 g palladium(II) chloride (5 mmoles), 50 ml water, 50 ml chlorobenzene, 0.7 g (1.8 mmoles) hexadecyltrimethylammonium bromide as the surfactant component, and other components described in Table I. The reactor was pressured to 30 psig (207 kPa) with oxygen and heated to 105° C. The reaction was continued for 5 hours with intermittent pressuring with oxygen as described above. Other components of the catalyst system utilized in the runs of this example and the results obtained in the runs (by glc analysis) are presented in Table I below.

TABLE I

| Run No. | $CuCl_2$, mmole | $H_3BO_3$, mmole | LiCl, mmole | 1-Hexene Conversion, % | Selectivity[a], % | 2-Hexanone[b], % |
|---|---|---|---|---|---|---|
| 1 | 20 | 100 | — | 61 | 91 | 76 |
| 2 | 20 | 100 | 100 | 63 | 100 | 100 |
| 3 | 20 | — | — | 51 | 99 | 68 |
| 4 | — | 100 | — | 27 | 80 | 61 |

[a]Selectivity to hexanones.
[b]Amount of 2-hexanone in ketone mixture.

The results of Run I demonstrate operability of this invention with a catalyst system comprising palladium(II) chloride, cupric chloride, and orthoboric acid for the two-phase oxidation of 1-hexene to a mixture of 2- and 3-hexanones. The additional presence of lithium chloride (Run 2) results in the conversion of the 1-hexene to 2-hexanone only. Oxidation in the absence of orthoboric acid (Run 3) or cupric chloride (Run 4) results in a lower conversion of 1-hexene than in the invention Run 1.

EXAMPLE II

A control run (Run 5) was carried out in the same type of apparatus and with the same components and general procedures as described for Run 2 of Example I, except that the orthoboric acid was replaced with 60 mmoles of hydrogen chloride. No oxygen uptake was observed with this catalyst system and no hexanones were found in the reaction mixture. This indicates tht the orthoboric acid in the two-phase oxidation of this invention behaves in a considerably different manner than the HCl used in conventional Wacker oxidation reactions.

EXAMPLE III

Two runs were carried out in which 2-hexene was oxidized to a mixture of 2-hexanone and 3-hexanone. In each run the reactor was charged with 2-hexene (200 mmoles), palladium(II) chloride (5 mmoles), cupric chloride (20 mmoles), water (50 ml), chlorobenzene (50 ml), and hexadecyltrimethylammonium bromide (1.8 mmoles). These reactions were carried out utilizing the same apparatus and procedure as described above. Other components of the catalyst systems utilized in the two runs of this example and the results obtained in the runs (by glc) are presented in Table II below.

TABLE II

| Run No. | $H_3BO_3$, mmole | LiCl, mmole | 2-Hexene Conversion, % | Selectivity[a], % | 2-Hexanone[b], % |
|---|---|---|---|---|---|
| 6 | 100 | — | 70 | 80 | 64 |
| 7 | — | 100 | 8 | 64 | 53 |

[a]See footnote (a) of Table I.
[b]See footnote (b) of Table I.

The results of these runs indicate that 2-hexene can be oxidized to a mixture of 2-hexanone and 3-hexanone in high conversion and high selectivity to ketones with the catalyst system of this invention (Run 6), while replacing the orthoboric acid with lithium chloride (Run 7) results in a very low conversion of 2-hexene under the conditions used.

EXAMPLE IV

Two runs were carried out in which neohexene (3,3-dimethyl-1-butene) was oxidized to pinacolone (3,3-dimethyl-2-butanone). In each run neohexene, palladium(II) chloride (5 mmoles), cupric chloride (20 mmoles), water (50 ml), chlorobenzene (50 ml), and hexadecyltrimethylammonium bromide (1.8 mmoles) were charged to the reactor. Each run was conducted in the same manner as described above except the extraction solvent for Run 8 was benzene instead of ether. Other components of the catalyst system and amounts of neohexane utilized in the two runs of this example and the results obtained (by glc) are presented in Table III below.

TABLE III

| Run No. | $H_3BO_3$, mmole | LiCl, mmole | Neohexene, mmole | Neohexene Conversion, % | Pinacolone,[a] % |
|---|---|---|---|---|---|
| 8 | 100 | — | 200 | 49 | 66 |
| 9 | — | 100 | 212 | 20 | 29 |

[a]Amount of pinacolone in product mixture.

The result obtained in Run 8 demonstrates operability of the process of this invention for the oxidation of neohexene to pinacolone. The result of Run 9 indicates that replacement of orthoboric acid with lithium chloride results in a significantly lower conversion than in invention Run 8.

EXAMPLE V

Three runs were conducted in which 1-hexene was oxidized using catalyst systems with low levels of halides. In each run 1-hexene (200 mmoles), palladium(II) acetate (5 mmoles), water (50 ml), chlorobenzene (50 ml), and hexadecyltrimethylammonium bromide (1.8 mmoles) were charged to the reactor. These runs utilized the same apparatus and procedure as described above for Run 1, except that the reaction time was 6 hours and in Runs 11 and 12 sodium chloride was added to the ether-water mixture during product isolation to prevent emulsion formation and allow phase separation. The other components of the catalyst system utilized in the runs of this example and the results obtained in the runs (by glc analysis) are shown in Table IV below.

TABLE IV

| Run No. | $Cu(OAc)_2$, mmole | $H_3BO_3$, mmole | 1-Hexene Conversion, % | Selectivity(a), % | 2-Hexanone(b), % |
|---|---|---|---|---|---|
| 10 | 10 | 75 | 24 | 77 | 81 |
| 11 | — | 100 | 38 | 53 | 100 |
| 12 | — | 100 | 18 | 11 | (c) |

(a)See footnote (a) of Table I.
(b)See footnote (b) of Table I.
(c)Not determined.

The result of Run 10 indicates that the palladium(II) chloride and cupric chloride of the catalyst system of Run 1 can be replaced with the corresponding acetates to obtain a low-halide system which should have low-corrosion properties. However, the hexene conversion observed under the conditions used was lower than in a similar run using the chlorides (Run 1). Two other runs (Runs 11 and 12) without copper catalyst component showed erratic conversions. The reason for the variations in results is not known, but may be a result of emulsion problems encountered during the ether-water separation.

EXAMPLE VI

Several runs were carried out in which 2-butene was oxidized to methyl ethyl ketone. The apparatus and general procedure described before Example I were utilized in these runs. In each run the reactor was charged with the indicated amount of 2-butene (a mixture of cis- and trans-isomers), palladium(II) chloride (5 mmoles), cupric chloride (20 mmoles), hexadecyltrimethylammonium bromide (1.8 mmoles), water (50 ml), and chlorobenzene (50 ml). The amounts of orthoboric acid and 2-butene and the reaction temperatures utilized in these runs, as well as the results obtained in the runs (by glc analysis) are presented in Table V below.

TABLE V

| Run No. | $H_3BO_3$, mmole | 2-Butene mmole | Temp. °C. | 2-Butene Conversion, % | Methyl Ethyl Ketone, (a) % | 3-Chloro-2-Butanone,(b) % |
|---|---|---|---|---|---|---|
| 13 | 100 | 202 | 105 | 93 | 75 | 7.2 |
| 14 | 100 | 200 | 90 | 98 | 82 | 2 |
| 15 | 100 | 207 | 75 | 93 | 94 | trace |
| 16 | 100 | 211 | 60 | 52 | 100 | — |
| 17 | — | 205(c) | 105 | 66 | 84 | 10 |
| 18 | — | 204 | 75 | 82 | 94 | — |

TABLE V-continued

| Run No. | H₃BO₃, mmole | 2-Butene mmole | Temp. °C. | 2-Butene Conversion, % | Methyl Ethyl Ketone, (a) % | 3-Chloro-2-Butanone,(b) % |
|---|---|---|---|---|---|---|
| 19 | — | 214 | 60 | 71 | 100 | — |

(a) Amount of methyl ethyl ketone in the reaction product based on the amount of 2-butene converted.
(b) Amount of 3-chloro-2-butanone in the reaction product based on the amount of 2-butene converted.
(c) The reaction mixture also contained 100 mmoles sodium chloride.

The results of Runs 13 through 16 demonstrate operability of the process of this invention for the two-phase oxidation of 2-butene to methyl ethyl ketone at reaction temperatures from about 60° C. to about 105° C. 3-Chloro-2-butanone is a by-product of this reaction at higher reaction temperatures. Control Runs 17, 18, and 19 without the presence of orthoboric acid result in lower 2-butene conversions than the corresponding runs with orthoboric acid except at 60° C.

EXAMPLE VII

Two runs were carried out in which 1-butene was oxidized to methyl ethyl ketone at a reaction temperature of 60° C. The apparatus and general procedure described before Example I were utilized in these runs. In each run, the reactor was charged with the indicated amounts of 1-butene, palladium(II) chloride (5 mmoles), cupric chloride (20 mmoles), hexadecyltrimethylammonium bromide (1.8 mmoles), water (50 ml), and chlorobenzene (50 ml). The amounts of orthoboric acid and 1-butene utilized in these runs and the results obtained in the runs (by glc analysis) are presented in Table VI below.

TABLE VI

| Run No. | H₃BO₃, mmole | 1-Butene mmole | 1-Butene Conversion, % | Methyl Ethyl Ketone (a), % |
|---|---|---|---|---|
| 20 | 100 | 209 | 57 | 100 |
| 21 | — | 216 | 65 | 100 |

(a) Amount of methyl ethyl ketone in the reaction product based on the amount of 1-butene converted.

In agreement with the results of runs with 2-butene at 60° C. in Example VI (Runs 16 and 19), the oxidation of 1-butene to methyl ethyl ketone at 60° C. occurs with a lower conversion of 1-butene with orthoboric acid (Run 20) than without (Run 21). However, based on results with 2-butene (Runs 15 and 18 of Example VI), it is believed that at higher reaction temperatures a higher conversion of 1-butene would occur with orthoboric acid than without orthoboric acid.

EXAMPLE VIII

Two control runs for the 2-butene oxidation reaction were carried out utilizing the same type of apparatus and general procedure described in the earlier runs. Run 22 was carried out in the same manner as in Run 16 of Example VI, except that a copper component of the catalyst system was not present. The absence of a copper component resulted in a decrease in 2-butene conversion from 52% in Run 16 to 16% in Run 22 and a decrease in the yield of methyl ethyl ketone from 100% to 39% (both based on the amount of 2-butene converted). These results indicate the importance of the copper component in the oxidation reaction of this invention.

Run 23 was carried out in a 1-liter glass-lined autoclave. The autoclave was charged with 2-butene (1.286 moles), palladium(II) chloride (10 mmoles), cupric chloride (40 mmoles), orthoboric acid (200 mmoles), water (200 ml), pentane (200 ml), and hexadecyltrimethylammonium bromide (3.6 mmoles). This run was carried out at 75° C. in a manner similar to Run 15 of Example VI, except that pentane was used as the organic phase of the two-phase system instead of chlorobenzene. At the conclusion of the usual 5 hours reaction time, only 11% of the 2-butene had reacted and methyl ethyl ketone was present in a yield of only 52% based on the amount of 2-butene converted. A comparison of these results with the results of Run 15 (93% conversion of 2-butene and a 94% yield of methyl ethyl ketone) shows the importance of the nature of the organic phase of the two-phase system of this invention.

EXAMPLE IX

Several runs were carried out to show the effect of the level of orthoboric acid on the oxidation of 2-butene under otherwise the same conditions as used in Run 15. In each run, the reactor was charged with palladium(II) chloride (5 mmoles), cupric chloride (20 mmoles), the indicated amount of orthoboric acid, water (50 ml), chlorobenzene (50 ml), hexadecyltrimethylammonium bromide (1.8 mmoles) and the indicated amount of 2-butene. In each run, the reaction was conducted for 5 hours at 75° C. The amounts of orthoboric acid and 2-butene utilized in each reaction and the results obtained in the runs (by glc analysis) are presented in Table VII below.

TABLE VII

| Run No. | H₃BO₃, mmole | 2-Butene, mmole | 2-Butene Conversion, % | Methyl Ethyl Ketone, (a) % Yield |
|---|---|---|---|---|
| 24 | 25 | 221 | 65 | 100 |
| 25 | 50 | 216 | 92 | 99 |
| 26 | 75 | 205 | 74 | 100 |
| 27 | 100 | 200 | 87 | 93 |
| 28 | 150 | 212 | 80 | 86 |
| 29 | 200 | 196 | 74 | 100 |
| 30 | 250 | 207 | 86 | 93 |

(a) Amount of methyl ethyl ketone in the product based on the amount of 2-butene converted.

The results described in Table VIi demonstrate the wide range of orthoboric acid level that can be utilized in the oxidation of this invention with high conversion and high selectivity to methyl ethyl ketone.

EXAMPLE X

A 1-liter glass-lined autoclave was charged with palladium(II) chloride (10 mmoles), cupric chloride (40 mmoles), orthoboric acid (200 mmoles), hexadecyltrimethylammonium bromide (3.6 mmoles), water (200 ml), chlorobenzene (200 ml), and 2-butene (1.375 moles). The autoclave was pressured to 30 psig with oxygen and heated to 75° C. At the end of the 4-hour reaction period the autoclave was cooled and vented and the reaction mixture was analyzed by the procedure described before Example I. 75% of the 2-butene charged to the autoclave had reacted, and the oxidation product contained methyl ethyl ketone in a yield of 65% based on the amount of 2-butene converted. No 3-chloro-2-butanone was observed.

The result of this run (Run 31) demonstrates operability of this invention utilizing palladium(II) chloride, cupric chloride, and orthoboric acid for the two-phase oxidation of 2-butene to methyl ethyl ketone.

EXAMPLE XI

A series of runs were carried out to demonstrate the use of the instant invention for the selective oxidation of the 1- and 2-butenes in a $C_4$ refinery stream with substantially no oxidation of the isobutylene. Each run was carried out using the same apparatus and procedure as described before Example I. In each run the reactor was charged with palladium(II) chloride (5 mmoles), cupric chloride (20 mmoles), hexadecyltrimethylammonium bromide (1.8 mmoles), water (50 ml), chlorobenzene (50 ml), and a synthetic butene mixture which contained 25% isobutylene, 34.3% 1-butene, 24.6% trans-2-butene, and 16.1% cis-2-butene.

In Run 32 the reaction mixture contained 100 mmoles of orthoboric acid and 202 mmoles of the synthetic butene mixture. At the end of the 5-hour reaction period (at 75° C.), analysis of the reaction mixture showed that 63% of the butene stream had been reacted. The product contained 127 mmoles of methyl ethyl ketone, a trace of 2-methyl-2-propanol, and no 3-chloro-2-butanone. If the isobutylene in the original mixed butene stream was not oxidized under the conditions used (this is suggested by the lack of oxidation products from isobutylene), the conversion of straight chain butenes would be 84% and the yield of methyl ethyl ketone would be 99.8% based on the amount of linear butenes converted.

In Run 33 the reaction mixture contained 100 mmoles of orthoboric acid and 218 mmoles of the synthetic butene mixture. At the conclusion of a 5-hour reaction period at 75° C., the unreacted butene mixture was collected and analyzed, and was found to contain:

| | |
|---|---|
| Isobutylene | 85.82% |
| 1-Butene | 0.02% |
| cis-2-Butene | 4.49% |
| trans-2-Butene | 9.69% |

The reaction product contained 132 mmoles of methyl ethyl ketone, a trace of 2-methyl-2-propanol, and no 3-chloro-2-butanone. The results of Runs 32 and 33 show that oxidation of a mixed butene stream with a catalyst system of this invention results in a selective oxidation of the 1-and 2-butenes with very little oxidation of isobutylene.

In Run 34 the reaction mixture contained 200 mmoles of the synthetic butene mixture and 100 mmoles of sodium chloride. This run did not contain orthoboric acid. At the conclusion of the 5-hour reaction period at 105° C., the reaction mixture was analyzed to show that 68% of the butene mixture had reacted. The reaction product contained 92 mmoles of methyl ethyl ketone, 24 mmoles of 2-methyl-2-propanol, and 14 mmoles of 3-chloro-2-butanone. The result of Run 34 shows that the use of sodium chloride instead of orthoboric acid in the oxidation of a mixed butene stream results in the hydration of isobutylene to 2-methyl-2-propanol.

In Run 35 the reaction mixture contained 204 mmoles of the synthetic butene mixture and did not contain orthoboric acid. At the conclusion of the 5-hour reaction period (at 75° C.), the reaction mixture was analyzed and the conversion of the butene stream was found to be 60%. The reaction product contained methyl ethyl ketone and acetone in a mole ratio of about 3/1. The result of Run 35 shows that the oxidation of a mixed butene stream in the absence of the orthoboric acid component of the catalyst system of this invention resulrts in substantial oxidation of the isobutylene.

EXAMPLE XII

Run 36 was carried out to demonstrate the selective oxidation of 1-butene to methyl ethyl ketone with the catalyst system of this invention in the presence of isobutylene with very little reaction of isobutylene. This reaction was carried out utilizing the same apparatus and procedure as described above. The reactor was charged with palladium(II) chloride (5 mmoles), cupric chloride (20 mmoles), orthoboric acid (100 mmoles), hexadecyltrimethylammonium bromide (1.8 mmoles), water (50 ml), chlorobenzene (50 ml), 1-butene (102 mmoles), and isobutylene (104 mmoles). Oxidation at 75° C. for 5 hours resulted in a 33% conversion of the butene mixture. The unreacted butenes were analyzed and were found to contain 92.56 weight % isobutylene, 0.06 weight % 1-butene, 1.18 weight % cis-2-butene, 2.04 weight % trans-2-butene, 3.44 weight % heavies, and several other compounds in minor amounts. Some isomerization of 1-butene to 2-butenes apparently occurred under the conditions of the reaction. The oxidation product contained methyl ethyl ketone in a yield of 99% based on the amount of converted reactant and a trace of 2-methyl-2-propanol. The result of this run demonstrates the use of the catalyst system of this invention for the selective, two-phase oxidation of 1-butene with only a trace reaction of isobutylene. This reaction provides a valuable method for the one-step purification of isobutylene from a mixture of isobutylene with linear butenes.

Reasonable variations and modificatitons are possible within the scope of the foregoing disclosure and the appended claims to the invention.

I claim:

1. A process for separating isobutylene from a $C_4$ stream containing isobutylene and linear mono-olefins by selectively oxidizing the linear olefins to leave isobutylene which comprises contacting:
   (a) said $C_4$ stream with
   (b) oxygen in
   (c) a reaction diluent comprising at least two liquid phases wherein at least one liquid phase is an aqueous phase, and in the presence of
   (d) a catalyst comprising a palladium component, a copper component, and a boron-containing material that provides a catalytically active boric acid under the conditions employed in the reaction, and
   (e) a surfactant selected from the group of:
      (1) quaternary ammonium salts of the general formula $(R''')_4N^+X^-$,
      (2) alkali metal alkyl sulfates of the general formula $R'''OSO_3M$,
      (3) alkali metal salts of alkanoic acids of the general formula $R'^vCO_2M$,
      (4) alkali metal salts of alkaryl sulfonic acids of the general formula

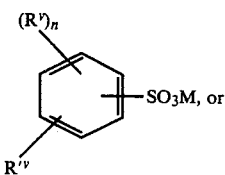

(5) 1-alkyl pyridinium salts of the general formula

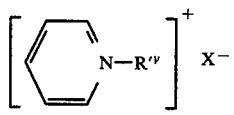

wherein R''' is an alkyl radical of from 1 to 20 carbon atoms and wherein the total number of carbon atoms in said quaternary ammonium salt is from about 8 to about 30 carbon atoms; $X^-$ is selected from the group consisting of $Br^-$, $Cl^-$, $I^-$, $F^-$, $R'''CO_2^-$, $QSO_3^-$, $BF_4^-$, $HSO_4^-$, wherein Q is an aryl or alkaryl radical of 6 to 10 carbon atoms; $R'^v$ is an alkyl radical of from 10 to about 20 carbon atoms; M is an alkali metal; $R^v$ is an alkyl radical of 1 to 4 carbon atoms and wherein n is 0 or an integer of from 1 to 4, under oxidation conditions sufficient to oxidize the linear monoolefins of (a) to carbonyl compounds, and then separating the oxidation products resulting from the oxidation of the linear mono-olefins from the unreacted isobutylene.

2. A process as in claim 1 wherein the palladium and copper of said catalyst is palladium(II) acetate and cupric acetate.

3. A process as in claim 1 wherein:
the molar ratio of the boric acid to palladium is about 0.2:1 to about 100:1;
the molar ratio of said olefinic hydrocarbon reactant to palladium is about 5:1 to about 1,000:1;
the molar ratio of said surfactant to the palladium is about 0.01:1 to about 10:1;
the pressure of oxygen in the reaction system is in the range of from about 2 to about 250 psig above the autogeneous pressure at the temperature utilized;
said reaction temperature is in the range of about 20° C. to about 200° C.

4. A process as in claim 1 wherein said diluent consists of two phases, one aqueous and the other an organic phase wherein said organic phase is relatively inert to the oxidation conditions employed, inert to hydrolysis-type reactions, and shows a limited solubility in the aqueous phase.

5. A process as in claim 4 wherein the amount of organic diluent of the two-phase diluent is in the range of about 20 to about 0.2 volumes of organic diluent to one volume of olefinic hydrocarbon reactant and the amount of aqueous phase is in the range of about 20 to about 0.2 volumes per volume of olefinic hydrocarbon reactant.

6. A process as in claim 4 wherein said organic diluent is chlorobenzene.

7. A process as in claim 1 wherein:
said diluent is an aqueous phase and an organic phase with the organic phase being chlorobenzene;
said catalyst comprises palladium(II) chloride, cupric chloride, and orthoboric acid; and
said surfactant is hexadecyltrimethylammonium bromide.

8. A process as in claim 1 wherein said catalyst further comprises a halide of an alkali metal or an alkaline earth metal.

9. A process as in claim 8 wherein the molar ratio of halide ion derived from the alkali metal or alkaline earth metal halide to the palladium component is from about 5:1 to about 1,000:1.

10. A process in accordance with claim 1 wherein said reaction temperature is greater than 60° C.

* * * * *